(12) United States Patent
Akimoto et al.

(10) Patent No.: US 11,740,214 B2
(45) Date of Patent: Aug. 29, 2023

(54) SENSOR AND SENSOR MODULE

(71) Applicant: KABUSHIKI KAISHA TOSHIBA, Tokyo (JP)

(72) Inventors: Yosuke Akimoto, Yokohama Kanagawa (JP); Hiroki Kudo, Kawasaki Kanagawa (JP); Hiroaki Yamazaki, Yokohama Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 242 days.

(21) Appl. No.: 17/176,799

(22) Filed: Feb. 16, 2021

(65) Prior Publication Data
US 2021/0318282 A1    Oct. 14, 2021

(30) Foreign Application Priority Data

Apr. 10, 2020   (JP) .................. 2020-071085

(51) Int. Cl.
*G01N 33/00*         (2006.01)

(52) U.S. Cl.
CPC ..... *G01N 33/0045* (2013.01); *G01N 33/0073* (2013.01)

(58) Field of Classification Search
CPC .................. G01N 33/0009; G01N 33/0073
See application file for complete search history.

(56) References Cited

U.S. PATENT DOCUMENTS

| 2008/0175759 A1* | 7/2008 | Oishi ............... G01N 27/125 |
| | | 422/98 |
| 2020/0083549 A1 | 3/2020 | Kawai et al. |

FOREIGN PATENT DOCUMENTS

| JP | H11-101705 A | 4/1999 | |
| JP | 2011-209192 A | 10/2011 | |
| JP | 2015-12504 A | 1/2015 | |
| WO | WO 2018/110441 A1 | 6/2018 | |
| WO | WO-2019069616 A1 * | 4/2019 | ............. G01D 21/00 |

OTHER PUBLICATIONS

Machine translation of WO-2019069616 (Year: 2019).*

* cited by examiner

*Primary Examiner* — Nathaniel J Kolb
(74) *Attorney, Agent, or Firm* — Finnegan, Henderson, Farabow, Garrett & Dunner, LLP

(57) ABSTRACT

According to one embodiment, a sensor includes a handhole part, a sensor module, and a holder. The handhole part includes an inner wall. The sensor module is provided in the handhole part. The sensor module includes a housing, a sensor circuit provided in the housing, the sensor circuit including a gas sensor element, and a battery configured to supply electrical power to the sensor circuit. The holder holds the sensor module so that a gap is formed between the inner wall and the housing and between the housing and a first member under the housing.

14 Claims, 11 Drawing Sheets

SENSOR AND SENSOR MODULE

CROSS-REFERENCE TO RELATED APPLICATIONS

This application is based upon and claims the benefit of priority from Japanese Patent Application No. 2020-071085, filed on Apr. 10, 2020; the entire contents of which are incorporated herein by reference.

FIELD

Embodiments described herein relate generally to a sensor and a sensor module.

BACKGROUND

For example, there is a sensor that detects a gas such as hydrogen, etc. More stable operation of the sensor is desirable.

DETAILED DESCRIPTION

Figure 1:
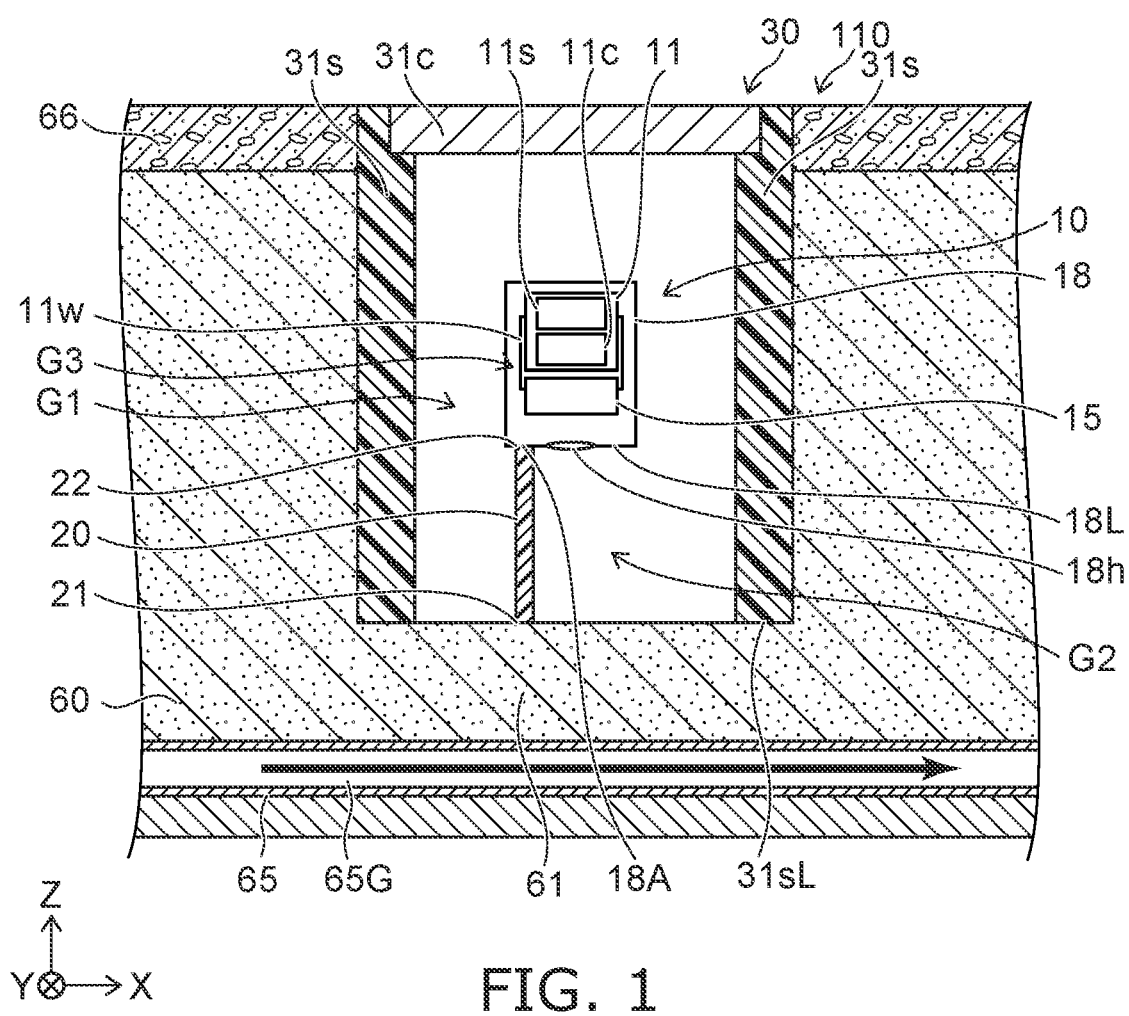
FIG. 1 is a schematic cross-sectional view illustrating a sensor according to a first embodiment.

According to one embodiment, a sensor includes a handhole part, a sensor module, and a holder. The handhole part includes an inner wall. The sensor module is provided in the handhole part. The sensor module includes a housing, a sensor circuit provided in the housing, the sensor circuit including a gas sensor element, and a battery configured to supply electrical power to the sensor circuit. The holder holds the sensor module so that a gap is formed between the inner wall and the housing and between the housing and a first member under the housing.

According to one embodiment, a sensor module includes a housing including a held portion, a sensor circuit including a gas sensor element provided in the housing, and a battery configured to supply electrical power to the sensor circuit. The sensor module is capable of being located in the handhole part by the held portion being held so that a gap is formed between the housing and an inner wall of the handhole part and between the housing and a first member under the housing.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

FIG. 1 is a schematic cross-sectional view illustrating a sensor according to a first embodiment.

As shown in FIG. 1, the sensor 110 according to the embodiment includes a handhole part 30, a sensor module 10, and a holder 20.

For example, the handhole part 30 is buried in an installation object 60. The installation object 60 is a ground surface, a floor, a wall, etc. The handhole part 30 includes, for example, an inner wall 31s and a lid part 31c. The inner wall 31s is, for example, tubular. For example, the lid part 31c is in the same layer as a surface layer 66 (which may be, for example, paving, etc.) of the installation object 60.

The direction in which the inner wall 31s extends is taken as a Z-axis direction. One direction perpendicular to the Z-axis direction is taken as an X-axis direction. A direction perpendicular to the Z-axis direction and the X-axis direction is taken as a Y-axis direction.

The handhole part 30 is, for example, circular (including flattened-circular) in the X-Y plane. According to the embodiment, the planar shape of the handhole part 30 is arbitrary.

The sensor module 10 is located in the handhole part 30. The sensor module 10 includes a housing 18, a sensor circuit 11, and a battery 15. The sensor circuit 11 is located in the housing 18. The sensor circuit 11 includes a gas sensor element 11s. For example, the gas sensor element 11s is configured to detect hydrogen. Thus, in one example, the sensor module 10 is configured to detect hydrogen. According to the embodiment, the sensor module 10 may be configured to detect another gas.

In the example, the sensor circuit 11 includes a control circuit 11c. The control circuit 11c controls the gas sensor element 11s. The control circuit 11c is, for example, a microcomputer.

The battery 15 is configured to supply electrical power to the sensor circuit 11. For example, the battery 15 and the sensor circuit 11 are electrically connected by wiring 11w.

The holder 20 holds the sensor module 10. In the example, a lower portion 21 of the holder 20 is fixed to a first member 61. The first member 61 is under the housing 18. The first member 61 is, for example, a ground surface. The first member 61 is, for example, at least one of a ground surface, a floor, or a wall. The sensor module 10 is held by an upper portion 22 of the holder 20. The housing 18 of the sensor module 10 includes a held portion 18A that is held by the holder 20. For example, the held portion 18A may include an unevenness or a recess that meshes with the holder 20, etc. The held portion 18A includes, for example, a resin. The thermal conductivity of the held portion 18A is low.

According to the embodiment, the holder 20 holds the sensor module 10 so that a gap is formed between the inner wall 31s and the housing 18 and between the housing 18 and the first member 61 under the housing 18. For example, a gap G1 is between the inner wall 31s and the housing 18. A gap G2 is between the housing 18 and the first member 61 under the housing 18. The gap G1 and the gap G2 are air. The housing 18 is separated from the inner wall 31s via the gap G1. The housing 18 is separated from the first member 61 via the gap G2.

For example, it was found that condensation easily occurs at the sensor module 10 located in the handhole part 30, etc. It is considered that this is caused by the reduction of the temperature of the sensor module 10 and around the sensor module 10. For example, the heat capacity of the first member 61 is large. For example, the temperature of the first member 61 becomes low at night, etc. The temperature of the inner wall 31s that contacts the first member 61 (the ground surface, etc.) also becomes low. For example, it is considered that condensation occurs at the sensor module 10 when the temperature of the sensor module 10 decreases as the temperature around the sensor module 10 decreases. In particular, when condensation occurs at the sensor circuit 11, misoperations of the sensor circuit 11 easily occur. For example, the value that is detected by the sensor circuit 11 easily becomes inaccurate.

According to the embodiment, the housing 18 of the sensor module 10 is separated from the inner wall 31s via the gap G1 and separated from the first member 61 via the gap G2. Therefore, the sensor module 10 is not thermally continuous with the surroundings. Even when the temperature of the surroundings decreases, the temperature of the sensor module 10 is not easily linked to the temperature of the surroundings. According to the embodiment, the electrical power from the battery 15 is supplied to the sensor circuit 11. The temperature of the sensor circuit 11 easily increases due to the supplied electrical power. Therefore, the condensation can be suppressed particularly around the sensor circuit 11. Because the condensation is suppressed, abnormal operations of the sensor circuit 11 can be suppressed. The values that are detected by the sensor circuit 11 are accurate. According to the embodiment, a sensor can be provided in which stable operations are possible.

For example, the temperature of the control circuit 11c increases particularly easily due to the electrical power supplied from the battery 15. Due to the heat of the control circuit 11c, the temperature of the gas sensor element 11s is prevented from becoming excessively low; and the condensation can be effectively suppressed.

As shown in FIG. 1, a gap G3 is provided between the housing 18 and the sensor circuit 11. Thereby, the sensor circuit 11 is thermally isolated from the housing 18. The temperature of the sensor circuit 11 is prevented from becoming low.

It is favorable for the thermal conductivity of the holder 20 holding the sensor module 10 to be low. For example, the holder 20 includes a resin. The thermal conduction between the sensor module 10 and the surroundings can be suppressed thereby.

As shown in FIG. 1, the housing 18 includes a lower part 18L. For example, the lower part 18L faces the first member 61. At least a portion of the bottom part of the handhole part 30 may be between the lower part 18L and the first member 61. The lower part 18L is higher than a lower end 31sL of the inner wall 31s. For example, the gap G2 is stably formed thereby. The lower part 18L includes a hole 18h. A gas can pass through the hole 18h.

For example, a gas pipe 65 is provided in the installation object 60. The sensor 110 is located on the gas pipe 65. A gas 65G passes through the gas pipe 65. When the gas 65G leaks from the gas pipe 65, the gas 65G reaches the sensor module 10 via the first member 61 of the installation object 60. The gas 65G can reach the sensor circuit 11 by passing through the hole 18h. The gas 65G is detected by the sensor circuit 11. The sensor 110 is configured to detect a gas leak.

Figure 2:
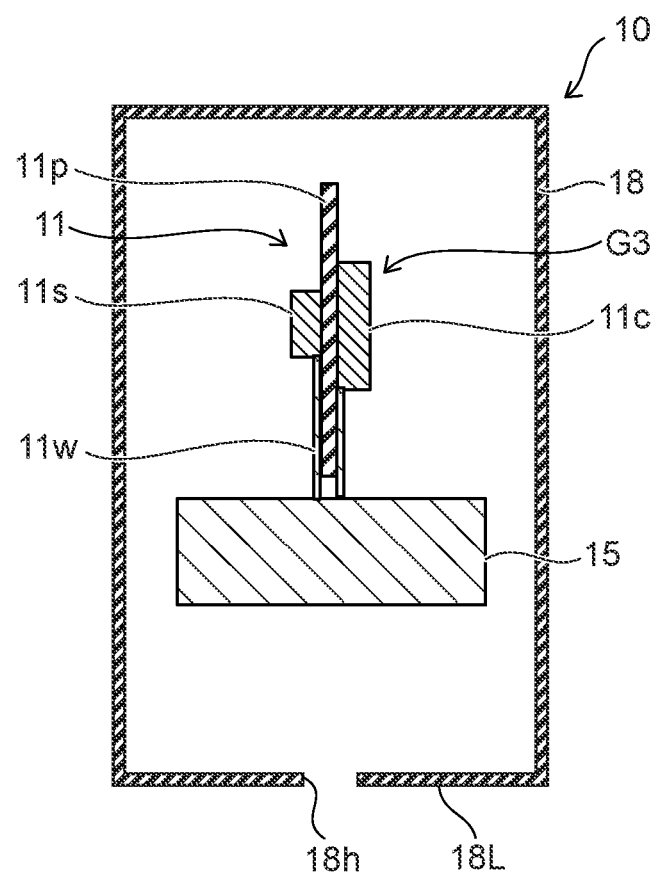
FIG. 2 is a schematic cross-sectional view illustrating the sensor according to the first embodiment.

FIG. 2 is a schematic cross-sectional view illustrating the sensor according to the first embodiment.

FIG. 2 shows one example of the sensor module 10. As shown in FIG. 2, the sensor circuit 11 may include a substrate 11p in addition to the gas sensor element 11s and the control circuit 11c. At least a portion of the substrate 11p is between the gas sensor element 11s and the control circuit 11c. For example, when the temperature of the control circuit 11c increases, the heat is easily conducted to the gas sensor element 11s. The condensation of the gas sensor element 11s can be more effectively suppressed.

Figure 3:
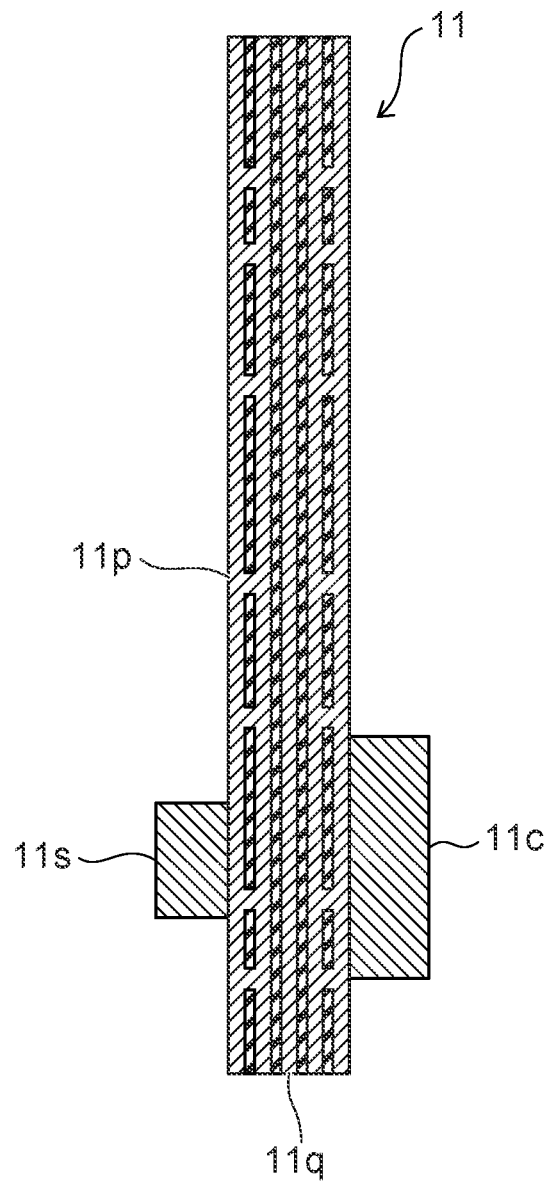
FIG. 3 is a schematic cross-sectional view illustrating the sensor according to the first embodiment.

FIG. 3 is a schematic cross-sectional view illustrating the sensor according to the first embodiment.

FIG. 3 shows one example of the sensor circuit 11. As shown in FIG. 3, at least a portion of the substrate 11p is between the gas sensor element 11s and the control circuit 11c. The substrate 11p includes an electrically-conductive layer 11q. The electrically-conductive layer 11q is, for example, a ground electrically-conductive layer. At least a portion of the electrically-conductive layer 11q is between the gas sensor element 11s and the control circuit 11c. The transmission of electrical noise between the gas sensor element 11s and the control circuit 11c is suppressed by providing the electrically-conductive layer 11q. In such a case as well, good thermal conduction is obtained between the gas sensor element 11s and the control circuit 11c.

Figure 4:
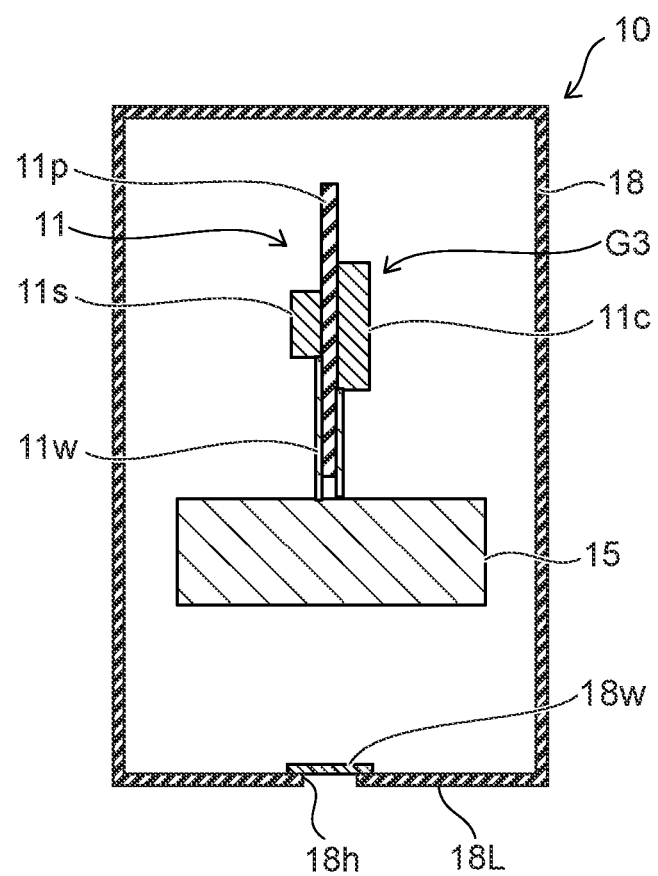
FIG. 4 is a schematic cross-sectional view illustrating the sensor according to the first embodiment.

FIG. 4 is a schematic cross-sectional view illustrating the sensor according to the first embodiment.

FIG. 4 shows one example of the sensor module 10. As shown in FIG. 3, the housing 18 may include a waterproof sheet 18w. The waterproof sheet 18w overlaps the hole 18h. The waterproof sheet 18w transmits a gas. The penetration of water into the housing 18 can be suppressed. More stable detection can be performed.

Several examples of sensors according to the embodiment will now be described. In the following description, a description is omitted for parts similar to those of the sensor 110.

Figure 5:
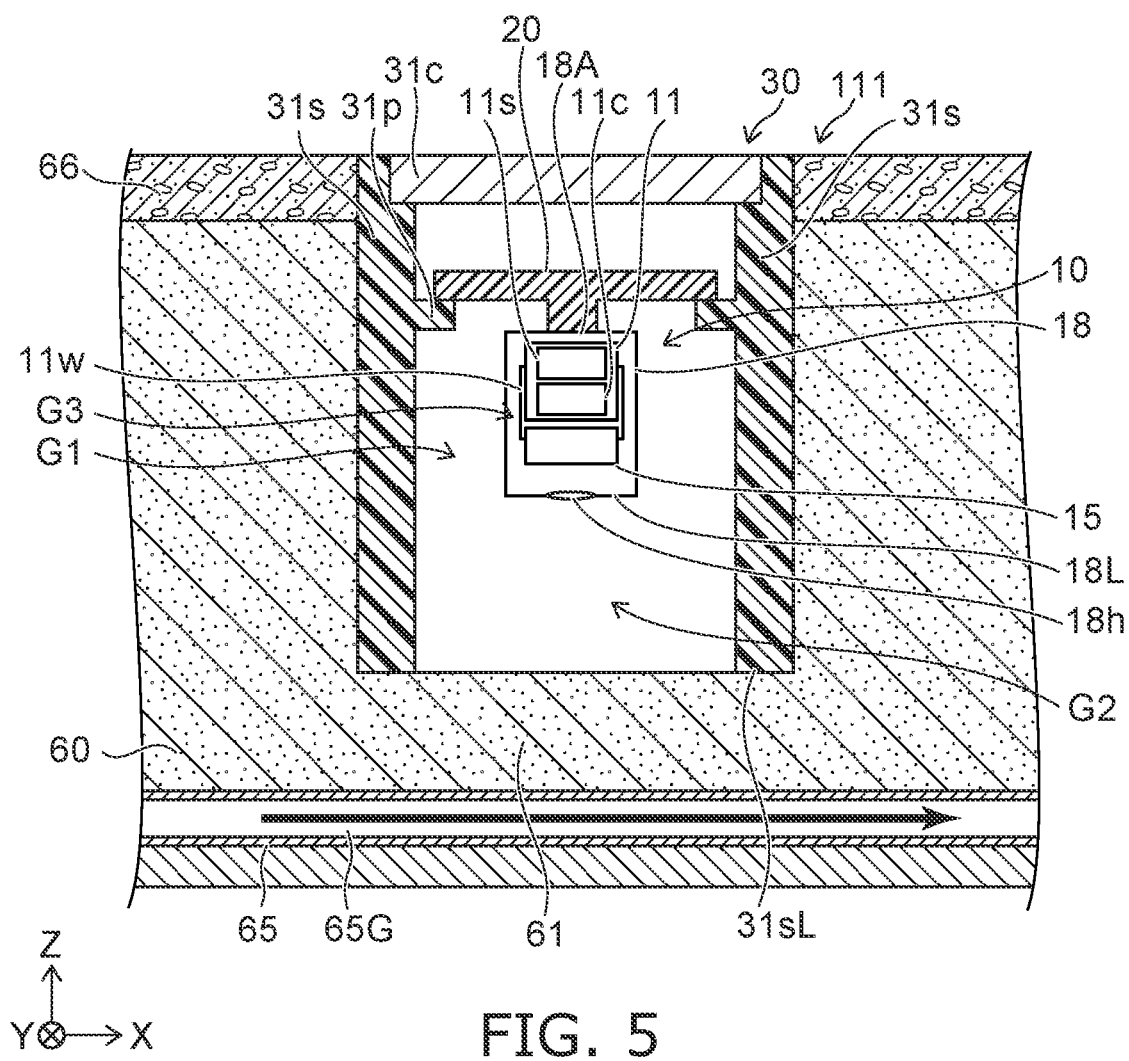
FIG. 5 is a schematic cross-sectional view illustrating a sensor according to the first embodiment.

FIG. 5 is a schematic cross-sectional view illustrating a sensor according to the first embodiment.

In the sensor 111 according to the embodiment as shown in FIG. 5, the holder 20 is held by the inner wall 31s. In the example, the inner wall 31s includes a protrusion 31p. A portion of the holder 20 is placed on the protrusion 31p. The holder 20 suspends the sensor module 10. In the example as well, for example, the gap G1 is between the inner wall 31s and the housing 18. The gap G2 is between the housing 18 and the first member 61 under the housing 18. The holder 20 may include, for example, a resin.

Figure 6:
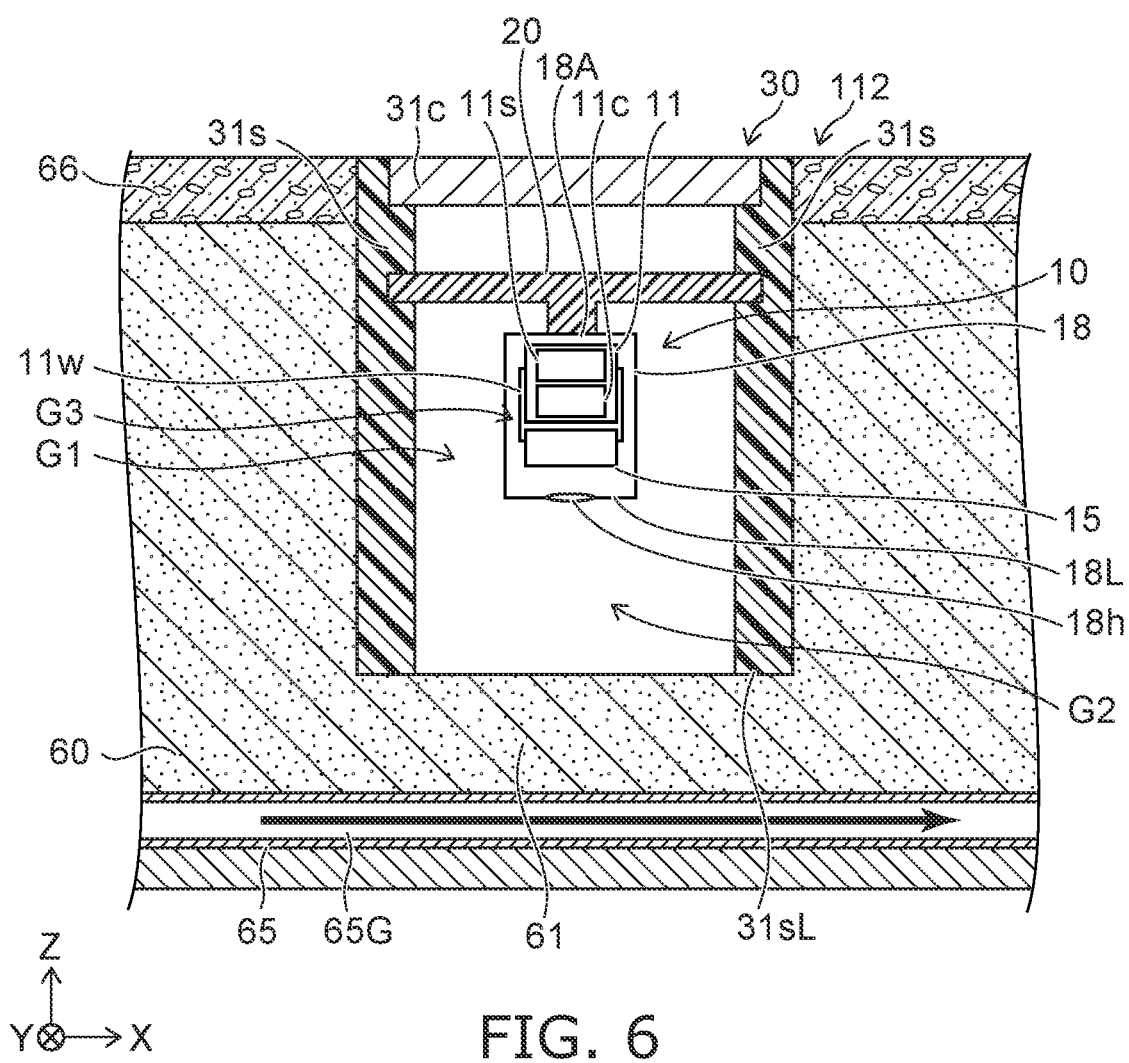
FIG. 6 is a schematic cross-sectional view illustrating a sensor according to the first embodiment.

FIG. 6 is a schematic cross-sectional view illustrating a sensor according to the first embodiment.

In the sensor 112 according to the embodiment as shown in FIG. 6 as well, the holder 20 is held by the inner wall 31s. In the example, an end of the holder 20 is buried in the inner wall 31s. The holder 20 suspends the sensor module 10. In the example as well, for example, the gap G1 is between the inner wall 31s and the housing 18. The gap G2 is between the housing 18 and the first member 61 under the housing 18. The holder 20 may include, for example, a resin.

Figure 7:
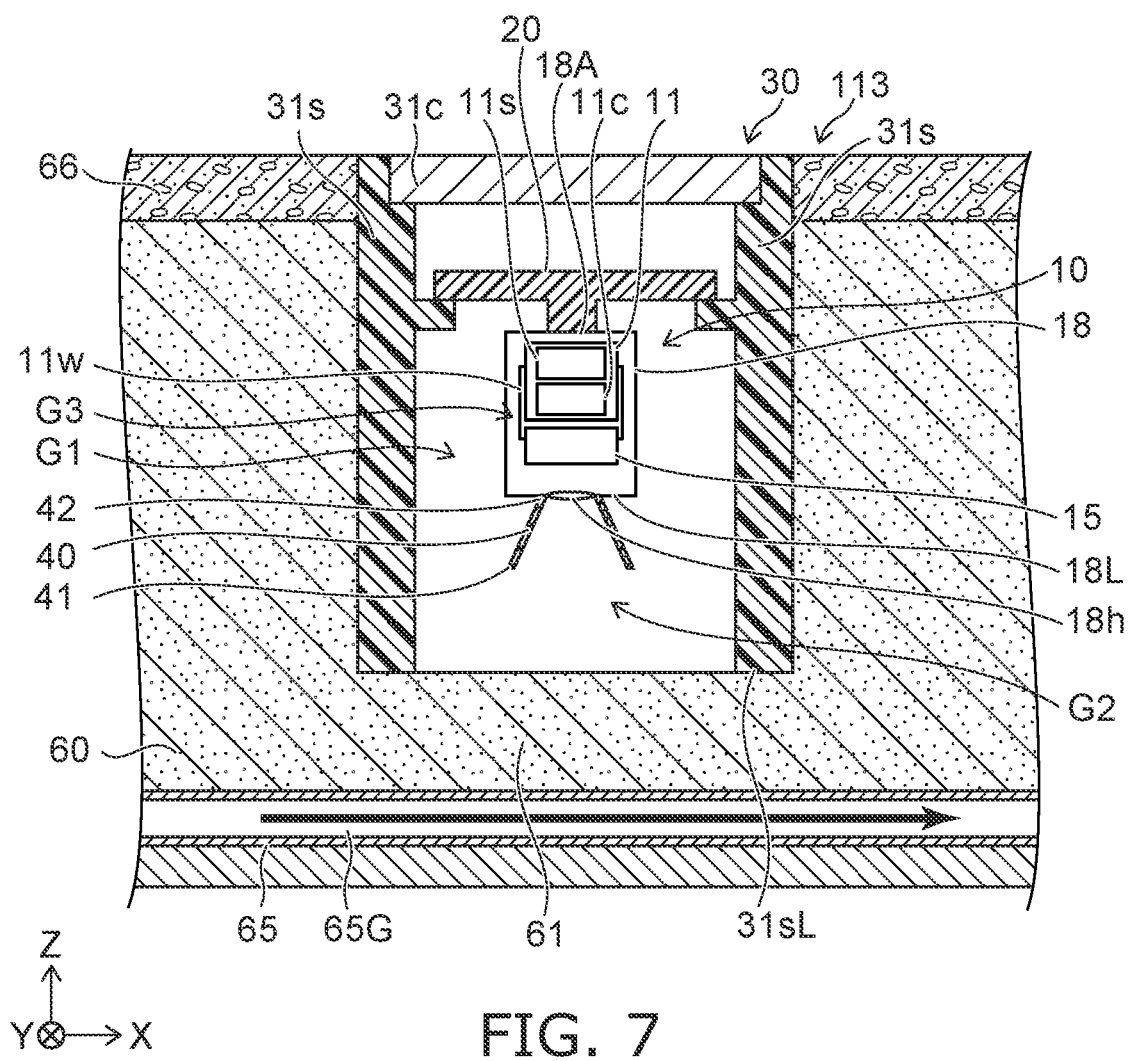
FIG. 7 is a schematic cross-sectional view illustrating a sensor according to the first embodiment.

FIG. 7 is a schematic cross-sectional view illustrating a sensor according to the first embodiment.

As shown in FIG. 7, the sensor 113 according to the embodiment includes a tubular part 40 in addition to the handhole part 30, the sensor module 10, and the holder 20. The tubular part 40 includes a first opening 41 and a second opening 42. The first opening 41 faces the first member 61. The second opening 42 faces the hole 18h. The first opening 41 is a lower opening. The second opening 42 is an upper opening. The surface area of the first opening 41 is greater than the surface area of the second opening 42. The gas 65G that leaks from the gas pipe 65 reaches the first opening 41 by passing through the first member 61. The gas 65G reaches the hole 18h by passing through the tubular part 40. Much of the gas 65G can be collected because the first opening 41 of the gas 65G is large. Detection with higher sensitivity is possible.

The position in the Z-axis direction of the first opening 41 may be the same as, higher than, or lower than the position in the Z-axis direction of the lower end 31sL of the inner wall 31s. In the example as well, for example, the gap G1 is between the inner wall 31s and the housing 18. The gap G2 is between the housing 18 and the first member 61 under the housing 18.

Figure 8:
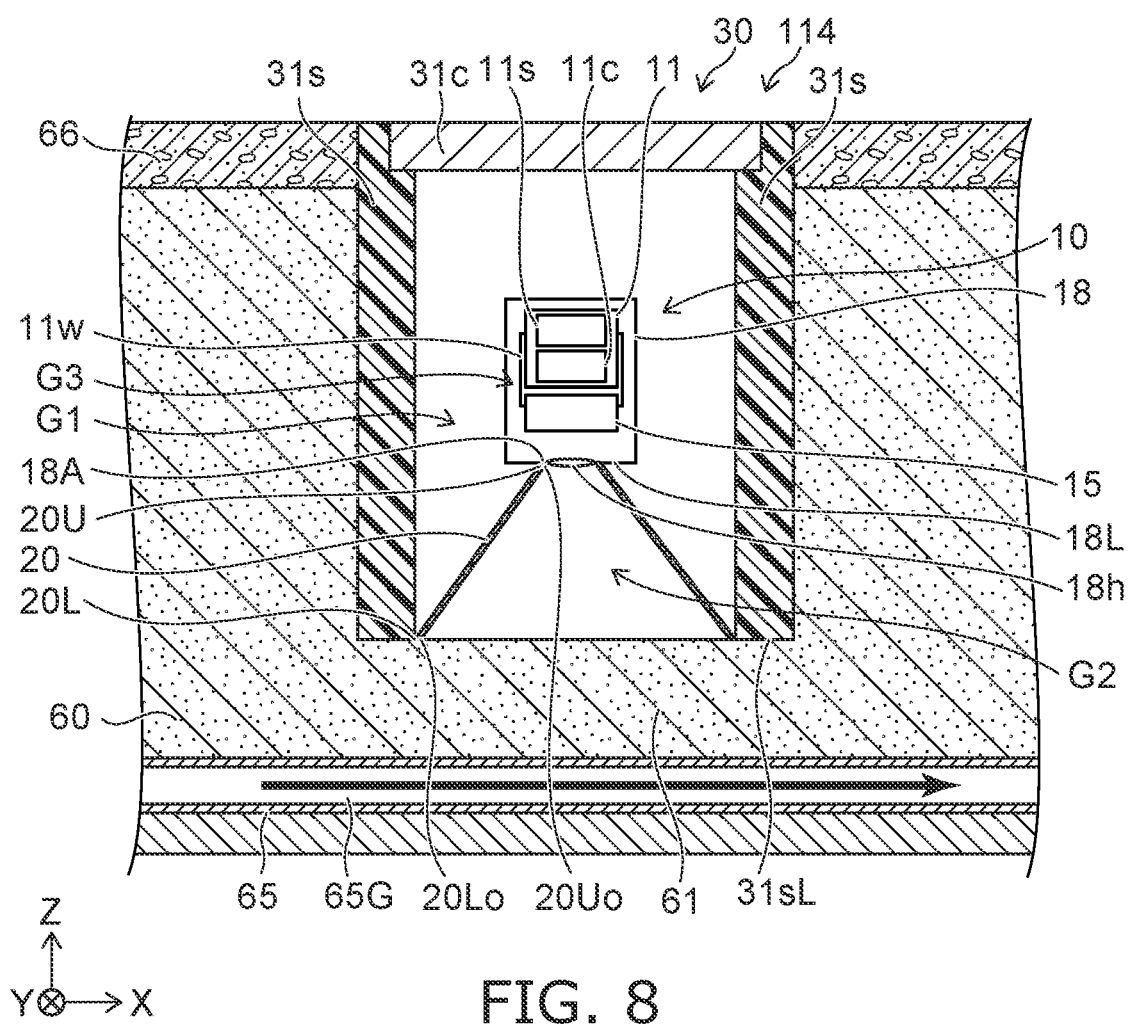
FIG. 8 is a schematic cross-sectional view illustrating a sensor according to the first embodiment.

FIG. 8 is a schematic cross-sectional view illustrating a sensor according to the first embodiment.

In the sensor 114 according to the embodiment as shown in FIG. 8, the holder 20 is tubular. The holder 20 includes a lower end portion 20L and an upper end portion 20U. An opening 20Lo of the lower end portion 20L faces the first member 61. An opening 20Uo of the upper end portion 20U faces the hole 18h. For example, the surface area of the opening 20Lo of the lower end portion 20L is greater than the surface area of the opening 20Uo of the upper end portion 20U. In addition to the function of holding the sensor module 10, the holder 20 has a function of collecting the leaked gas 65G. A sensor that has few components and stable operations can be provided. In the example as well, for example, the gap G1 is between the inner wall 31s and the housing 18. The gap G2 is between the housing 18 and the first member 61 under the housing 18. The holder 20 may include, for example, a resin.

Figure 9:
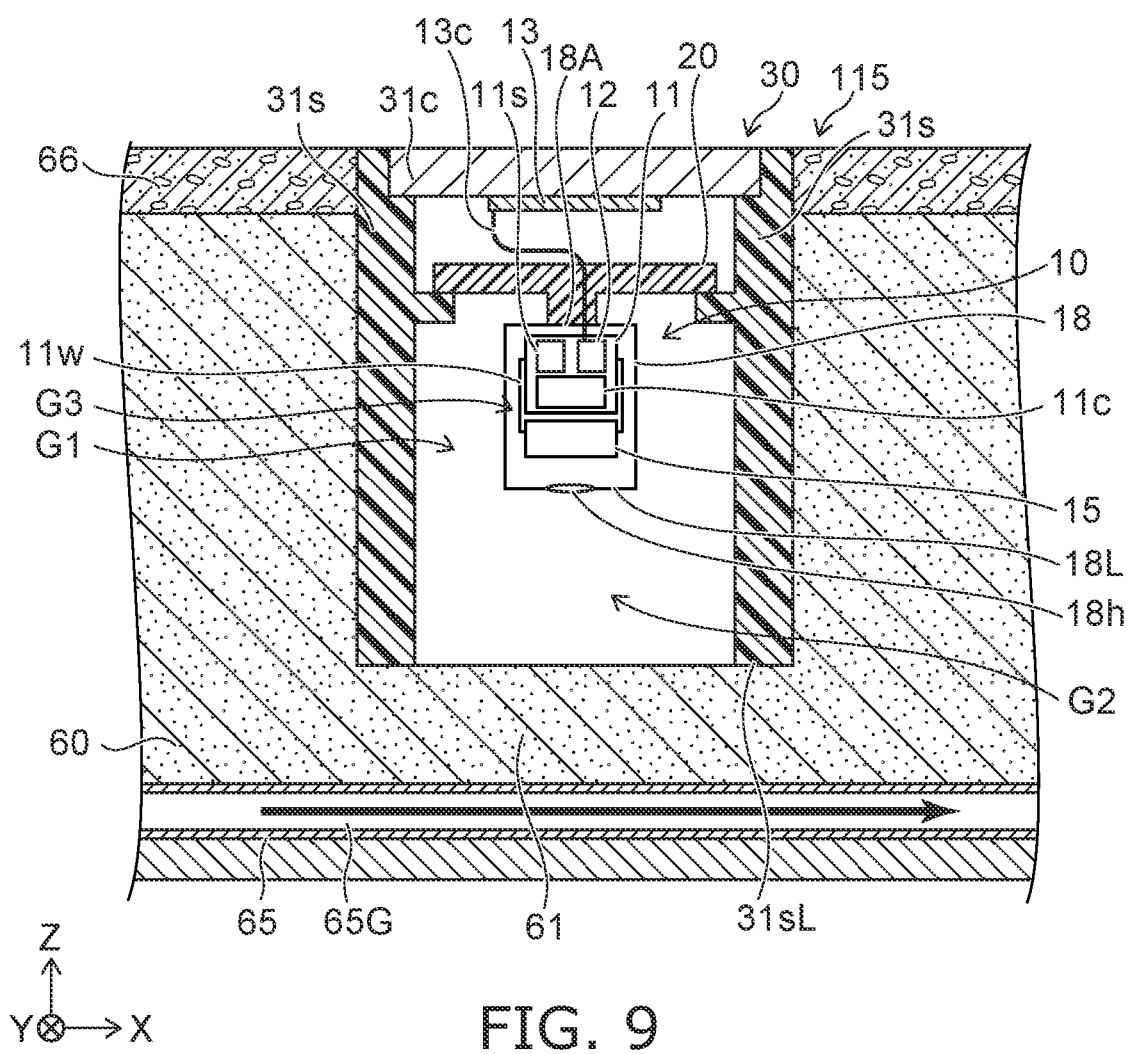
FIG. 9 is a schematic cross-sectional view illustrating a sensor according to the first embodiment.

FIG. 9 is a schematic cross-sectional view illustrating a sensor according to the first embodiment.

In the sensor 115 according to the embodiment as shown in FIG. 9, the sensor module 10 includes a wireless communication circuit 12. For example, the wireless communication circuit 12 is configured to transmit a signal corresponding to a value detected by the sensor circuit 11. The sensor module 10 may include an antenna 13. The antenna 13 is connected with the wireless communication circuit 12. For example, the connection is performed by a cable 13c. As shown in FIG. 9, the antenna 13 may be fixable to the lid part 31c of the handhole part 30. Better communication is possible thereby.

Figure 10:
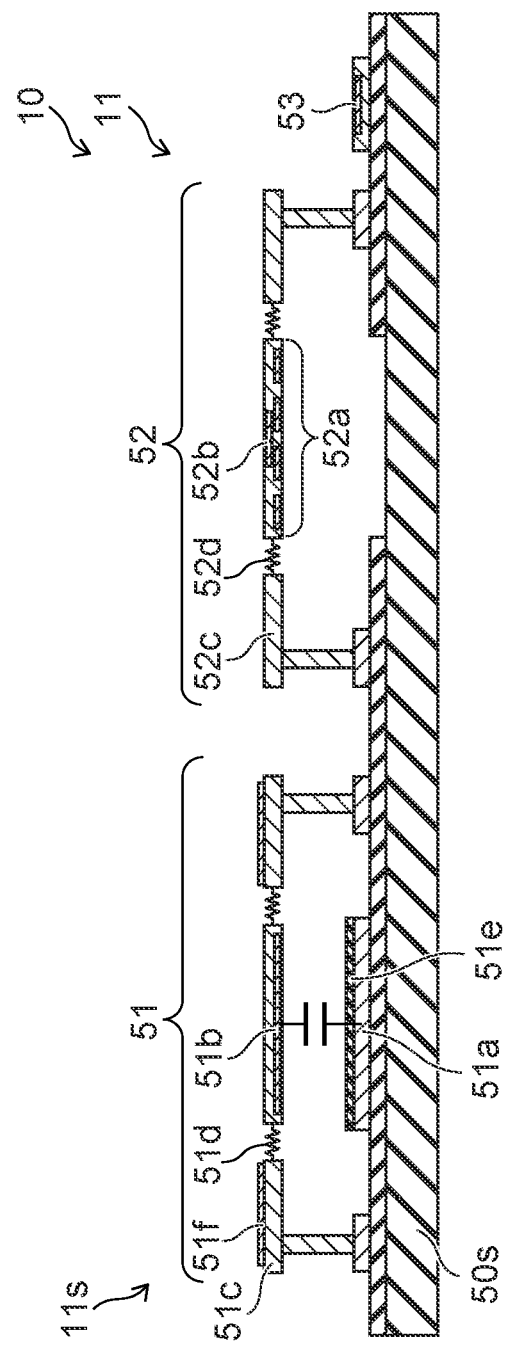
FIG. 10 is a schematic cross-sectional view illustrating a portion of the sensor according to the first embodiment.

FIG. 10 is a schematic cross-sectional view illustrating a portion of the sensor according to the first embodiment.

FIG. 10 illustrates a portion of the sensor module 10. In the sensor circuit 11 of the sensor module 10 as shown in FIG. 10, the gas sensor element 11s includes a first element 51.

The first element 51 includes a fixed electrode 51a, a movable electrode 51b, a holding member 51c, and a connection part 51d. The fixed electrode 51a and the holding member 51c are fixed to a base body 50s. One end of the connection part 51d is fixed to the holding member 51c. Another end of the connection part 51d is connected to the movable electrode 51b. The connection part 51d is, for example, a spring. The movable electrode 51b is held by the holding member 51c and the connection part 51d to be separated from the fixed electrode 51a. In the example, a film 51f is provided at the holding member 51c. The gas 65G to be detected can adsorb to the film 51f. For example, when the gas 65G adsorbs to the film 51f, physical characteristics of the film 51f change, and the distance between the movable electrode 51b and the fixed electrode 51a changes. The gas 65G to be detected can be detected by detecting the electrical capacitance between the movable electrode 51b and the fixed electrode 51a. The first element 51 is, for example, a capacitance change-type MEMS (Micro Electro Mechanical Systems) hydrogen sensor element.

The film 51f includes, for example, Pd, Cu, and Si. According to the embodiment, the material of the film 51f can be determined according to the type of the gas 65G to be detected.

In the example, an insulating film 51e is provided at the surface of the fixed electrode 51a. Contact of the movable electrode 51b with the fixed electrode 51a can be suppressed. More stable detection is possible.

In the example as shown in FIG. 10, the sensor module 10 includes a second element 52. The second element 52 includes a heater 52a, a temperature sensor 52b, a holding member 52c, and a connection part 52d. The holding member 52c is fixed to the base body 50s. One end of the connection part 52d is fixed to the holding member 52c. Another end of the connection part 52d is connected with the heater 52a and the temperature sensor 52b. The connection part 52d is, for example, a spring. For example, the connection part 52d has a high thermal resistance. The heater 52a and the temperature sensor 52b are held by the holding member 52c and the connection part 52d to be separated from the base body 50s. The heater 52a and the temperature sensor 52b correspond to a membrane part. The temperature of the membrane part that is locally heated by the heater 52a changes due to the thermal conductivity of the gas at the periphery of the membrane part. When the thermal conductivity of the gas to be detected is different from the thermal conductivity of the atmospheric gas, and when the concentration of the gas changes, the temperature of the membrane part changes, and the electrical resistance of the temperature sensor 52b located in the membrane part changes. For example, the thermal conductivity of hydrogen gas is greater than the atmospheric thermal conductivity. For example, the temperature of the membrane part is reduced by the concentration increase of hydrogen gas. By detecting the change of the electrical resistance, the change of the temperature can be detected, and hydrogen gas can be detected thereby. The second element 52 is, for example, a thermal conduction-type MEMS gas sensor element.

As shown in FIG. 10, the sensor module 10 (e.g., the sensor element 11s) may include a third element 53. The third element 53 is, for example, a temperature sensor. For example, the third element 53 is configured to detect the temperature of the environment.

For example, information that relates to the temperature of the sensor circuit 11 can be accurately known from the signal obtained from the second element 52 and the signal obtained from the third element 53. The gas 65G can be more accurately detected by correcting the value obtained from the first element 51 based on the signal obtained from the second element 52 and the signal obtained from the third element 53.

Thus, the sensor module 10 (e.g., the sensor element 11s) may include a temperature sensor (at least one of the second element 52 or the third element 53). The control circuit 11c (referring to FIG. 1) may correct the signal output from the gas sensor element 11s (e.g., the first element 51) based on a value detected by the temperature sensor.

For example, the correction may be performed outside the sensor module 10. In such a case, the sensor module 10 is configured to output a signal corresponding to the value detected by the gas sensor element 11s (e.g., the first element 51) and a signal corresponding to the value detected by the temperature sensor (e.g., at least one of the second element 52 or the third element 53). More accurate detection is possible by performing a correction using these output values.

As described above, the gas sensor element 11s may have a MEMS structure. A small sensor circuit 11 is obtained. For example, the space (e.g., the gap G3) around the sensor circuit 11 can be increased thereby, and the condensation, etc., can be further suppressed.

Figure 11:
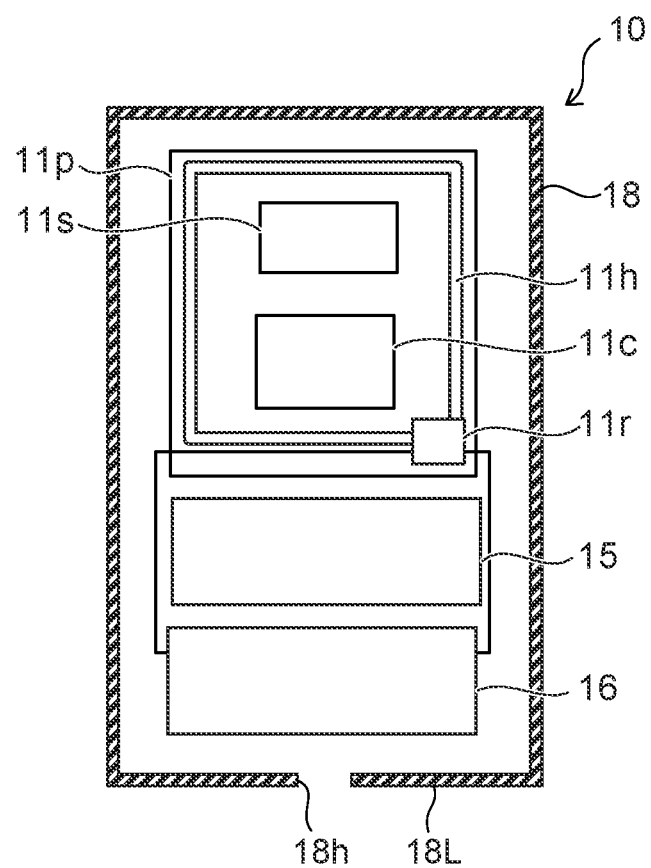
FIG. 11 is a schematic view illustrating a portion of the sensor according to the first embodiment.

FIG. 11 is a schematic view illustrating a portion of the sensor according to the first embodiment.

FIG. 11 illustrates the sensor module 10. As shown in FIG. 11, the sensor module 10 may include a heater 11h. The heater 11h is configured to heat at least a portion of the sensor circuit 11. For example, the heater 11h surrounds the gas sensor element 11s and the control circuit 11c.

In the example, a battery 16 is provided in addition to the battery 15. The temperature of the heater 11h is increased by the electrical power supplied from the battery 16. In the example, the output from the battery 16 is supplied to a heater controller 11r (e.g., a switch). The heater 11h is operated by a control of the heater controller 11r.

For example, there are cases where the output from the gas sensor element 11s is abnormal. At this time, there are cases where the abnormality can be restored by the heater 11h heating the gas sensor element 11s (e.g., the base body 50s).

For example, the remaining capacity of at least one of the battery 15 or the battery 16 may be detected by at least one of the control circuit 11c or the heater controller 11r. For example, the detection result may be transmitted via the wireless communication circuit 12. More stable operations are possible. The heater controller 11r may be, for example, a switch circuit. The heater controller 11r may be controlled by the control circuit 11c.

Second Embodiment

A second embodiment relates to the sensor module 10.

As shown in FIG. 1, the sensor module 10 includes the housing 18, the sensor circuit 11, and the battery 15. The housing 18 includes the held portion 18A. The held portion 18A is a part that is held by the holder 20. The sensor circuit 11 is located in the housing 18. The sensor circuit 11 includes the gas sensor element 11s. The battery 15 is configured to supply electrical power to the sensor circuit 11. The sensor module 10 is capable of being located in the handhole part 30 by the held portion 18A being held so that a gap (the gap G1 and the gap G2) is formed between the housing 18 and the inner wall 31s of the handhole part 30 and between the housing 18 and the first member 61 under the housing 18. According to the embodiment, for example, the condensation of the sensor circuit 11, etc., can be suppressed. A sensor module is provided in which stable operations are possible.

According to the embodiment, the sensor module 10 that is located in the handhole part 30 is fixed to be surrounded with an air layer. The sensor module 10 is thermally isolated from the handhole part 30 and the installation object 60 (e.g., soil). For example, the condensation of the sensor module 10 can be suppressed. For example, misdetection is suppressed.

Embodiments may include the following configurations (e.g., technological proposals).

Configuration 1

A sensor, comprising:
a handhole part including an inner wall;
a sensor module provided in the handhole part, the sensor module including
 a housing,
 a sensor circuit provided in the housing, the sensor circuit including a gas sensor element, and
 a battery configured to supply electrical power to the sensor circuit; and
a holder holding the sensor module so that a gap is formed between the inner wall and the housing and between the housing and a first member under the housing.

Configuration 2

The sensor according to Configuration 1, wherein
the first member is at least one of a ground surface, a floor, or a wall.

Configuration 3

The sensor according to Configuration 1 or 2, wherein
the holder includes a resin.

Configuration 4

The sensor according to any one of Configurations 1 to 3, wherein
the housing includes a lower part facing the first member, and
the lower part includes a hole through which a gas can pass.

Configuration 5

The sensor according to Configuration 4, wherein
the housing includes a waterproof sheet overlapping the hole.

Configuration 6

The sensor according to Configuration 4 or 5, further comprising:
a tubular part including a first opening and a second opening,
the first opening facing the first member,
the second opening facing the hole.

Configuration 7

The sensor according to Configuration 6, wherein
a surface area of the first opening is greater than a surface area of the second opening.

Configuration 8

The sensor according to Configuration 4 or 5, wherein
the holder is tubular,
an opening at a lower end portion of the holder faces the first member,
an opening at an upper end portion of the holder faces the hole, and
a surface area of the opening at the lower end portion is greater than a surface area of the opening at the upper end portion.

Configuration 9

The sensor according to any one of Configurations 1 to 7, wherein
a lower portion of the holder is fixed to the first member, and
the sensor module is held by an upper portion of the holder.

Configuration 10
 The sensor according to any one of Configurations 1 to 7, wherein
  the holder is held by the inner wall, and
  the holder suspends the sensor module.
Configuration 11
 The sensor according to any one of Configurations 1 to 10, wherein
  the sensor circuit further includes:
   a control circuit controlling the gas sensor element; and
   a substrate, and
  at least a portion of the substrate is between the gas sensor element and the control circuit.
Configuration 12
 The sensor according to Configuration 11, wherein
  the substrate includes an electrically-conductive layer, and
  at least a portion of the electrically-conductive layer is between the gas sensor element and the control circuit.
Configuration 13
 The sensor according to Configuration 11 or 12, wherein
  the sensor module includes a temperature sensor, and
  the controller corrects, based on a value detected by the temperature sensor, a signal output from the gas sensor element.
Configuration 14
 The sensor according to Configuration 11 or 12, wherein
  the sensor module includes a temperature sensor, and
  the sensor module is configured to output:
   a signal corresponding to a value detected by the gas sensor element; and
   a signal corresponding to a value detected by the temperature sensor.
Configuration 15
 The sensor according to any one of Configurations 10 to 14, wherein
  the gas sensor element has a MEMS structure.
Configuration 16
 The sensor according to any one of Configurations 1 to 15, wherein
  the sensor module includes a heater configured to heat at least a portion of the sensor circuit.
Configuration 17
 The sensor according to any one of Configurations 1 to 16, wherein
  the sensor module includes a wireless communication circuit.
Configuration 18
 The sensor according to Configuration 17, wherein
  the sensor module includes an antenna connected with the wireless communication circuit, and
  the antenna is fixable to a lid part of the handhole part.
Configuration 19
 The sensor according to any one of Configurations 1 to 18, wherein
  the sensor module is configured to detect hydrogen.
Configuration 20
 A sensor module, comprising:
  a housing including a held portion;
  a sensor circuit including a gas sensor element provided in the housing; and
  a battery configured to supply electrical power to the sensor circuit,
  the sensor module being capable of being located in the handhole part by the held portion being held so that a gap is formed between the housing and an inner wall of the handhole part and between the housing and a first member under the housing.

According to embodiments, a sensor and a sensor module can be provided in which stable operations are possible.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as handhole parts, sensor modules, housings, sensor circuits, batteries, holders, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors, and sensor modules practicable by an appropriate design modification by one skilled in the art based on the sensors, and the sensor modules described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:
1. A sensor, comprising:
 a handhole part including an inner wall;
 a sensor module provided in the handhole part, the sensor module including
  a housing,
  a sensor circuit provided in the housing, the sensor circuit including a gas sensor element, and
  a battery configured to supply electrical power to the sensor circuit; and
 a holder holding the sensor module so that a gap is formed between the inner wall and the housing and between the housing and a first member,
 wherein:
  the housing includes a lower part facing the first member,
  the lower part includes a hole through which a gas can pass,
  the holder is tubular,
  an opening at a lower end portion of the holder faces the first member,
  an opening at an upper end portion of the holder faces the hole, and
  a cross-sectional area of the opening at the lower end portion is greater than a cross-sectional area of the opening at the upper end portion.

2. The sensor according to claim 1, wherein the first member is at least one of a ground surface, a floor, or a wall.

3. The sensor according to claim 1, wherein the holder includes a resin.

4. The sensor according to claim 1, wherein the housing includes a waterproof sheet overlapping the hole.

5. The sensor according to claim 1, wherein the lower end portion of the holder is fixed to the first member, and the sensor module is held by the upper end portion of the holder.

6. The sensor according to claim 1, wherein the sensor circuit further includes:
   a control circuit controlling the gas sensor element; and
   a substrate, and
   at least a portion of the substrate is between the gas sensor element and the control circuit.

7. The sensor according to claim 6, wherein the substrate includes an electrically-conductive layer, and
   at least a portion of the electrically-conductive layer is between the gas sensor element and the control circuit.

8. The sensor according to claim 6, wherein the sensor module includes a temperature sensor, and
   the controller corrects, based on a value detected by the temperature sensor, a signal output from the gas sensor element.

9. The sensor according to claim 6, wherein the sensor module includes a temperature sensor, and
   the sensor module is configured to output:
   a signal corresponding to a value detected by the gas sensor element; and
   a signal corresponding to a value detected by the temperature sensor.

10. The sensor according to claim 1, wherein the gas sensor element has a MEMS structure.

11. The sensor according to claim 1, wherein the sensor module includes a heater configured to heat at least a portion of the sensor circuit.

12. The sensor according to claim 1, wherein the sensor module includes a wireless communication circuit.

13. The sensor according to claim 12, wherein the sensor module includes an antenna connected with the wireless communication circuit, and
    the antenna is fixable to a lid part of the handhole part.

14. The sensor according to claim 1, wherein the sensor module is configured to detect hydrogen.

\* \* \* \* \*